(12) United States Patent  
Gharpure et al.

(10) Patent No.: US 9,056,813 B2
(45) Date of Patent: Jun. 16, 2015

(54) PROCESS FOR PREPARATION OF FINGOLIMOD

(71) Applicants: Milind Gharpure, Pune (IN); Krishna Narawade, Mumbai (IN); Prem Chand, Panvel (IN); Shekhar Bhaskar Bhirud, Mumbai (IN)

(72) Inventors: Milind Gharpure, Pune (IN); Krishna Narawade, Mumbai (IN); Prem Chand, Panvel (IN); Shekhar Bhaskar Bhirud, Mumbai (IN)

(73) Assignee: Glenmark Generics Limited, Mumbai (IN)

( * ) Notice: Subject to any disclaimer, the term of this patent is extended or adjusted under 35 U.S.C. 154(b) by 0 days.

(21) Appl. No.: 14/373,214

(22) PCT Filed: Jan. 17, 2013

(86) PCT No.: PCT/IN2013/000034
§ 371 (c)(1),
(2) Date: Jul. 18, 2014

(87) PCT Pub. No.: WO2013/111162
PCT Pub. Date: Aug. 1, 2013

(65) Prior Publication Data
US 2015/0018578 A1    Jan. 15, 2015

Related U.S. Application Data

(60) Provisional application No. 61/702,850, filed on Sep. 19, 2012.

(30) Foreign Application Priority Data

Jan. 25, 2012 (IN) .............................. 254/MUM/2012
Jul. 9, 2012 (IN) .......................... 1972/MUM/2012

(51) Int. Cl.
C07C 209/78 (2006.01)
C07C 215/10 (2006.01)
(Continued)

(52) U.S. Cl.
CPC ............. *C07C 209/78* (2013.01); *C07C 303/28* (2013.01); *C07C 213/08* (2013.01);
(Continued)

(58) Field of Classification Search
None
See application file for complete search history.

(56) References Cited

U.S. PATENT DOCUMENTS 5,604,229 A * 2/1997 Fujita et al. ................. 514/252.1

OTHER PUBLICATIONS

Seidel et al., Journal of Organic Chemistry (2004), 69(11), pp. 3950-3952.*

*Primary Examiner* — Brian J Davis

(57) ABSTRACT

The present invention provides a process for preparation of fingolimod, a compound of Formula I or a pharmaceutically acceptable salt thereof, free of regioisomeric impurity compound of Formula IA.

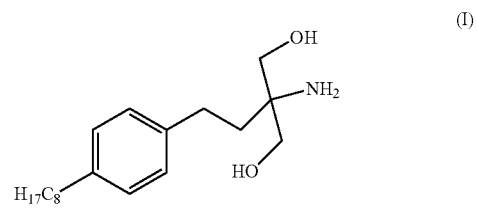

(I)

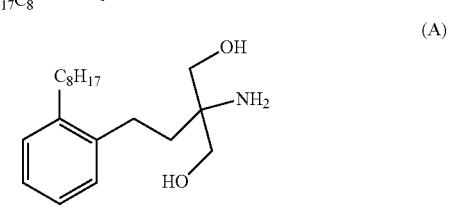

(A)

12 Claims, 3 Drawing Sheets

(51) Int. Cl.
*C07C 29/14* (2006.01)
*C07C 209/16* (2006.01)
*C07C 45/30* (2006.01)
*C07C 29/00* (2006.01)
*C07C 45/64* (2006.01)
*C07C 67/293* (2006.01)
*C07C 17/16* (2006.01)
*C07C 303/28* (2006.01)
*C07C 231/12* (2006.01)
*C07C 213/08* (2006.01)
*C07C 215/28* (2006.01)

(52) U.S. Cl.
CPC .............. *C07C215/28* (2013.01); *C07C 231/12* (2013.01); *C07C 17/16* (2013.01); *C07C 67/293* (2013.01); *C07C 45/64* (2013.01); *C07C 29/00* (2013.01); *C07C 29/14* (2013.01); *C07C 45/30* (2013.01); *C07C 209/16* (2013.01); *C07C 215/10* (2013.01)

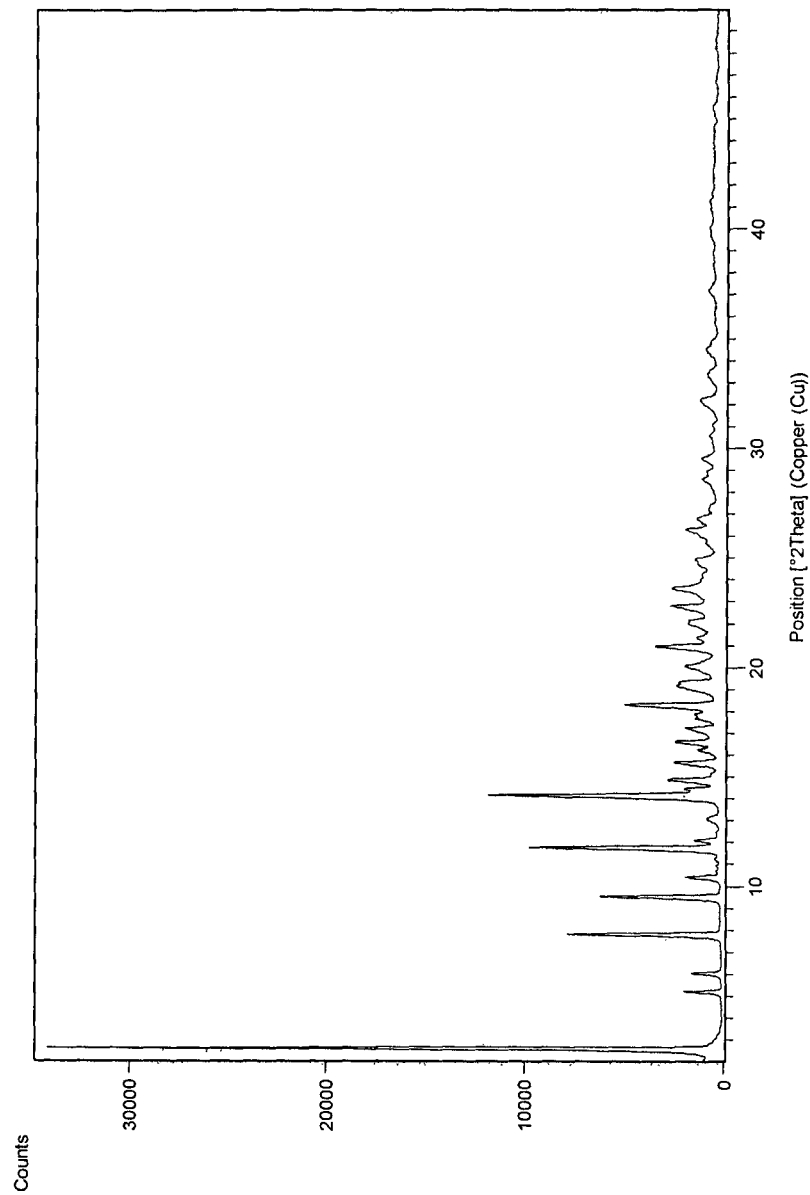
Fig 1 is an X-ray powder diffraction pattern of compound of Formula IX

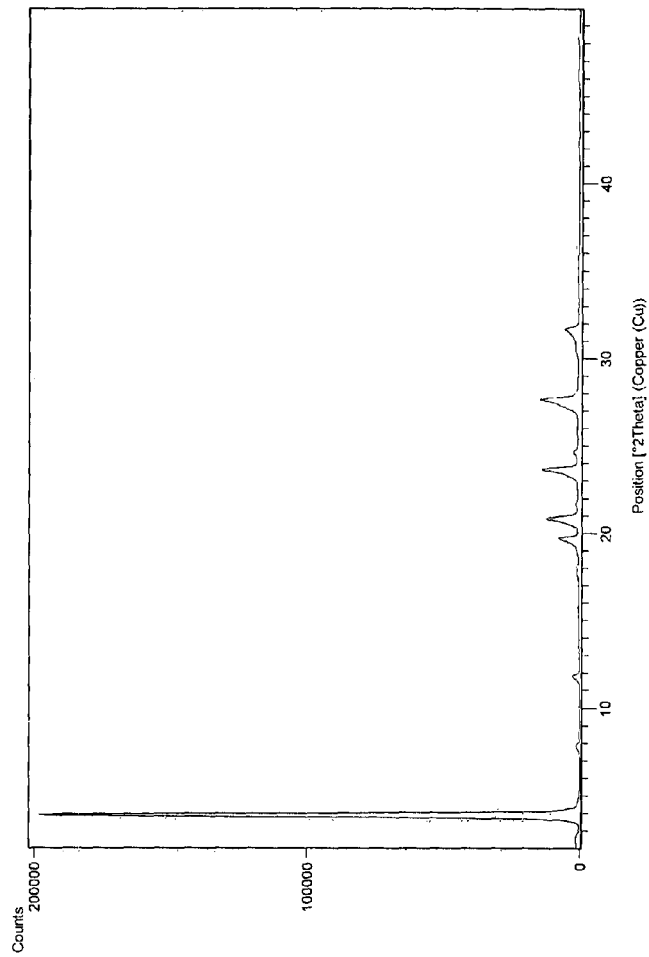
Fig. 2: is an X-ray powder diffraction pattern of compound of Formula I according to example 10a.

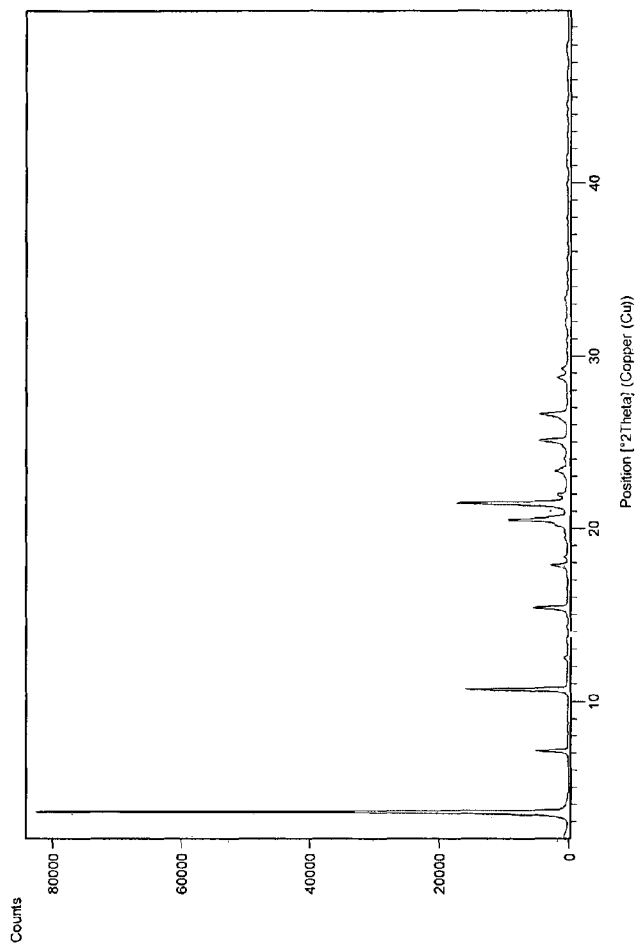
Fig.3: is an X-ray powder diffraction pattern of fingolimod hydrochloride according to example 11a.

PROCESS FOR PREPARATION OF FINGOLIMOD

PRIORITY

This application claims priority under 35U.S.C. §371 to International Application No. PCT/IN2013/000034, filed Jan. 17, 2013 which claims the benefit under 35 U.S.C. §119 to Indian Provisional Applications No. 254/MUM/2012, filed on Jan. 25, 2012, and Indian Provisional Application No. 1972/MUM/2012, filed on Jul. 9, 2012, U.S. Provisional Application No. 61/702,850, filed on Sept. 19, 2012 and entitled "PROCESS FOR THE PREPARATION OF FINGOLIMOD", the contents of which are incorporated by reference herein.

FIELD OF THE INVENTION

The present invention relates to a novel process for preparation of fingolimod and its pharmaceutical acceptable salt.

BACKGROUND OF THE INVENTION

Fingolimod, otherwise called FTY720, is an immunosuppressant, which is chemically known as 2-amino-2-[2-(4-octylphenyl)ethyl]propane-1,3-diol and is represented by Formula I:

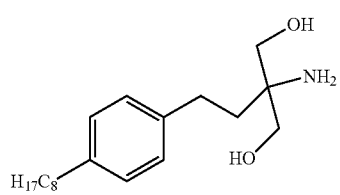

Formula I

Fingolimod hydrochloride is currently available as GILENYA® indicated for the treatment of patients with relapsing forms of multiple sclerosis.

U.S. Pat. No. 5,604,229 (U.S. Pat. No. '229) discloses fingolimod and the process for its preparation. Example 28 discloses a process for fingolimod with phenylethylacetate, compound of Formula II, as starting material.

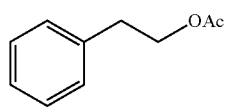

Formula II

The reaction involves acylation of compound of Formula II with octanoyl chloride by Friedel Crafts acylation. Friedel-Crafts acylation is one of the most important methods for manufacturing acylated benzene derivatives. The reaction typically utilizes an acylating agent and an electrophilic catalyst such as aluminum chloride, boron trifluoride, or hydrogen fluoride. A substituted benzene for example phenylethylacetate, compound of Formula II, as starting material would allow the acylation to potentially occur at different positions on the benzene ring relative to the substituent group. Consequently, in these cases, the reaction may lead to an undesirable mixture of isomeric products comprising both the compound of Formula III (desired compound) and its corresponding regioisomer a compound of Formula IIIA;

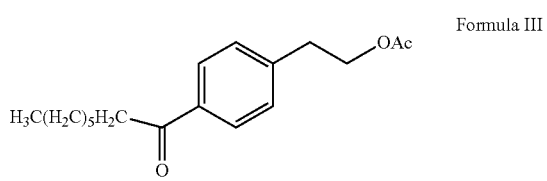

Formula III

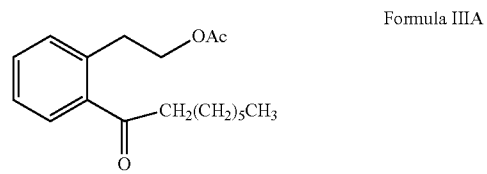

Formula IIIA

This co-production of the regioisomer is disadvantageous since it is structurally similar to the desired compound. The regioisomer compound of Formula IIIA, when present with the compound of Formula III, is expected to undergo a reaction similar to the compound of Formula III. These reactions, in turn, lead to the formation of regioisomeric impurity in each subsequent step that the compound of Formula III undergoes. These culminate to the detrimental formation of the regioisomeric impurity compound of Formula IA, which is difficult to separate from the desired compound fingolimod.

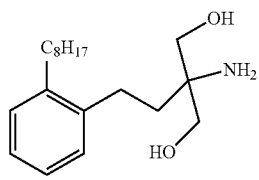

Formula IA

The process disclosed in U.S. Pat. No. '229 disadvantageously generates a set of corresponding regioisomeric impurities. Regioisomeric impurities reduce the yield of the desired product and often form by-products that substantially increase the difficulty of isolating the desired product in high purity. Here, in contrast, the present invention provides a novel process for the preparation of fingolimod, compound of Formula I, that is advantageously and substantially free of its regioisomeric impurity compound of Formula IA, via compound of Formula IV.

The process of the present invention for the preparation of fingolimod, compound of Formula I comprises hydrolysis of compound of Formula III, containing the regioisomeric impurity IIIA, and separating the resultant reaction mixture to obtain the compound of Formula IV, which is free of its regioisomeric impurity compound of Formula IVA.

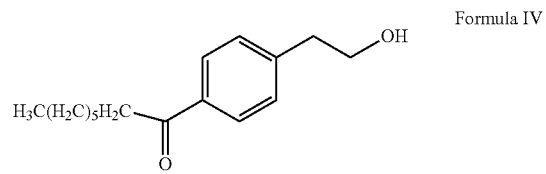

Formula IV

-continued

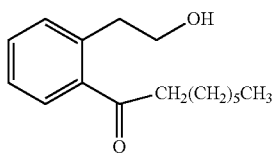
Formula IVA

The compound of Formula IV which is free of regioisomeric impurity compound of Formula IVA is then re-acetylated to obtain compound of Formula III. The compound of Formula III thus obtained is free of regioisomeric impurity compound of Formula IIIA.

The process of the present invention for the preparation of fingolimod, compound of Formula I provides fingolimod, compound of Formula I, which is substantially free of its regioisomeric impurity compound of Formula IA.

SUMMARY OF THE INVENTION

The present invention provides a process for preparation of fingolimod, a compound of Formula I or a pharmaceutically acceptable salt thereof, free of regioisomeric impurity compound of Formula IA

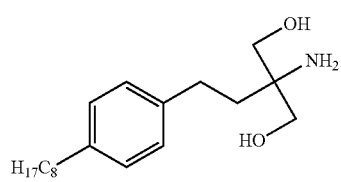
Formula I

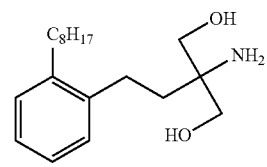
Formula IA the process comprising:
a. reacting a compound of Formula II with octanoyl halide to obtain a reaction mixture comprising a compound of Formula III and its corresponding regioisomer a compound of Formula IIIA;

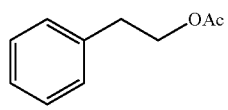
Formula II

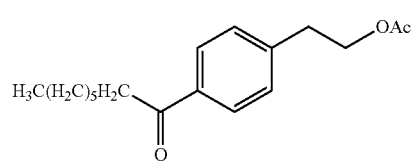
Formula III

-continued

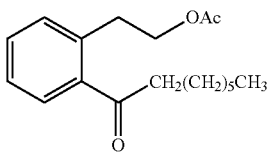
Formula IIIA a. hydrolyzing the reaction mixture resulting from step 'a' to obtain a reaction mixture comprising a compound of Formula IV and its corresponding regioisomer a compound of Formula IVA; and isolating the compound of Formula IV which is free of its regioisomeric impurity compound of Formula IVA;

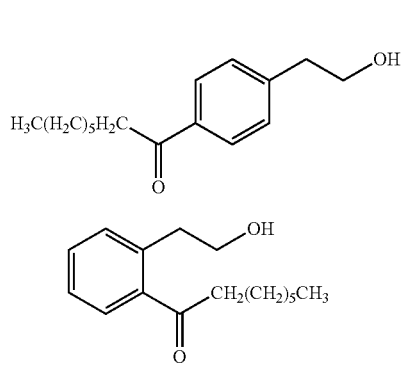
Formula IV

Formula IVA b. converting the compound of Formula IV resulting from step 'b' to a compound of Formula III by subjecting to acetylation;
c. converting the compound of Formula III to a compound of Formula VI by subjecting to reduction and deacetylation;

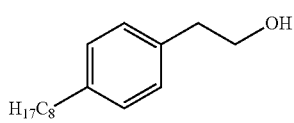
Formula VI d. converting the compound of Formula VI to a compound of Formula IX; and

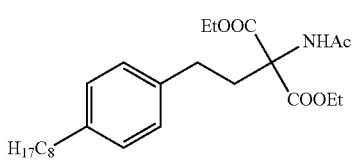
Formula IX e. converting the compound of Formula IX to fingolimod, compound of Formula I or pharmaceutically acceptable salt thereof.

The present invention provides use of compound of formula IV free of its regioisomeric impurity compound of Formula IVA for the preparation of fingolimod or a pharmaceutically acceptable salt thereof.

The present invention provides fingolimod or a pharmaceutically acceptable salt free of regioisomeric impurity compound of Formula IA or salt thereof.

The present invention provides a process for recrystallizing fingolimod hydrochloride by a solvent system comprising methanol and an ester solvent.

The present invention provides an isolated compound having the structure

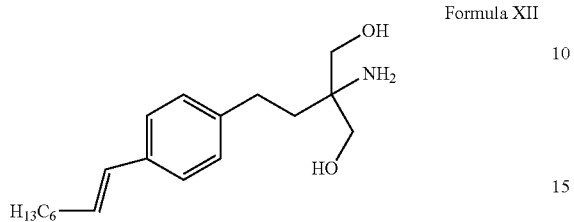

Formula XII

The present invention provides fingolimod or a pharmaceutically acceptable salt thereof wherein compound of Formula XII is present to an extent of less than 0.1% relative to the amount of fingolimod as determined by high performance liquid chromatography.

BRIEF DESCRIPTION OF THE FIGURES

FIG. 1: is an X-ray powder diffraction pattern of compound of Formula IX.

FIG. 2: is an X-ray powder diffraction pattern of compound of Formula I according to example 10a.

FIG. 3: is an X-ray powder diffraction pattern of fingolimod hydrochloride according to example: 11a.

DETAILED DESCRIPTION OF THE INVENTION

The present invention provides a process for preparation of fingolimod, a compound of Formula I or a pharmaceutically acceptable salt thereof, free of regioisomeric impurity compound of Formula IA

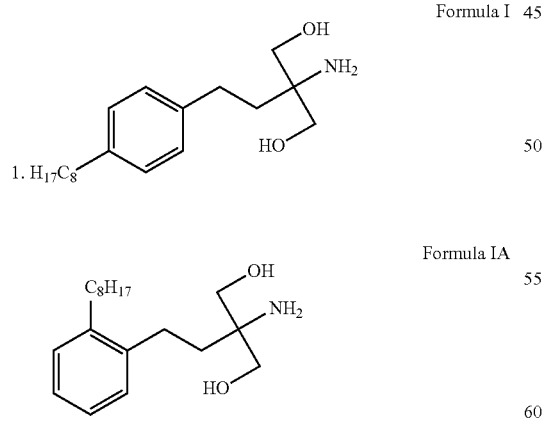

Formula I

Formula IA comprising:
a. reacting a compound of Formula II with octanoyl halide to obtain a reaction mixture comprising a compound of Formula III and its corresponding regioisomer a compound of Formula IIIA;

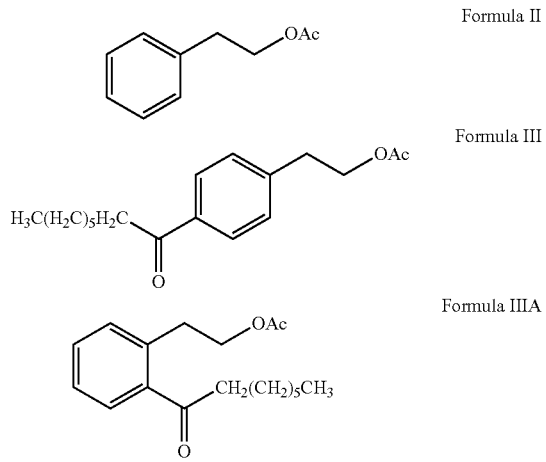

Formula II

Formula III

Formula IIIA b. hydrolyzing the reaction mixture resulting from step 'a' to obtain a reaction mixture comprising a compound of Formula IV and its corresponding regioisomer a compound of Formula IVA; and isolating the compound of Formula IV which is free of its regioisomeric impurity compound of Formula IVA;

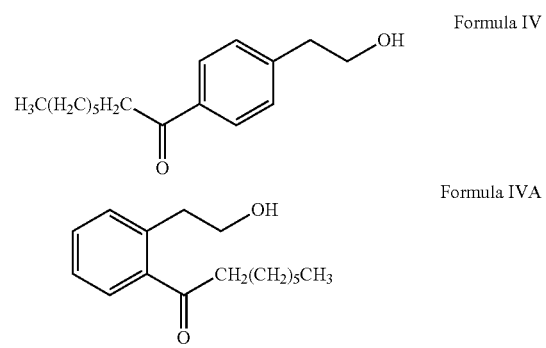

Formula IV

Formula IVA c. converting the compound of Formula IV resulting from step 'b' to a compound of Formula III by subjecting to acetylation;
d. converting the compound of Formula III to a compound of Formula VI by subjecting to reduction and deacetylation;

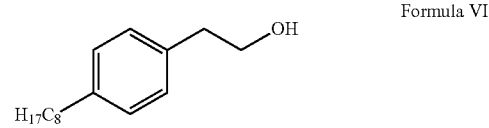

Formula VI e. converting the compound of Formula VI to a compound of Formula IX; and

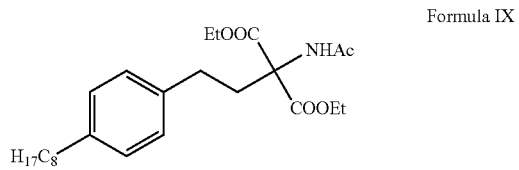

Formula IX f. converting the compound of Formula IX to fingolimod, compound of Formula I or pharmaceutically acceptable salt thereof.

The term "free of regioisomeric impurity" denotes that the regioisomeric impurity is present to the extent of less than 0.5%, preferably less than 0.2%.

In one embodiment, the present invention provides the regioisomeric impurity compound of Formula IA is present to the extent of 0.1%.

In one embodiment, the present invention provides the regioisomeric impurity compound of Formula IA is present to the extent of less than 0.1%, preferably absent.

In 'a' of the process directly described above, a compound of Formula II is reacted with octanoyl halide in the presence of a Lewis acid. The Lewis acid used is selected from the group consisting of boron trifluoride, aluminium chloride, ferric chloride and zinc bromide.

The octanoyl halide may be selected from the group consisting of octanoyl chloride, octanoyl bromide, octanoyl iodide and the like. Preferably octanoyl chloride.

The reaction of compound of Formula II with octanoyl halide may be carried out in the absence or presence of a solvent. The solvent may be selected from hydrocarbon or halogenated hydrocarbon solvent.

In one embodiment, the present invention provides the reaction of compound of Formula II with octanoyl halide carried out in presence of aluminium chloride and in the absence of a solvent.

After completion of the reaction, the product is isolated by extraction in an organic solvent. The organic solvent may be selected form halogenated hydrocarbons or acetate solvent. The product obtained contains the compound of Formula III and its corresponding regioisomer, a compound of Formula IIIA.

In 'b' of the process above, the product which is mixture of compound of Formula III and its corresponding regioisomer a compound of Formula IIIA is subjected to hydrolysis to obtain a reaction mixture comprising a compound of Formula IV and its corresponding regioisomer a compound of Formula IVA.

The hydrolysis may be carried out under acidic or basic reagents. The acidic reagents may be selected from inorganic acids such as hydrochloric acid, sulfuric acid and the like, and organic acids such as acetic acid and the like. The basic reagents for hydrolysis may be selected from hydroxides, carbonates and bicarbonates of alkali and alkaline earth metals for example, sodium hydroxide, potassium hydroxide, sodium carbonate, potassium carbonate, potassium bicarbonate and the like.

The hydrolysis may be carried out in the presence of water miscible organic solvents, as for example lower alcohols and the like.

In one embodiment of the present invention the mixture of compound of Formula III and its corresponding regioisomer a compound of Formula IIIA is subjected to basic hydrolysis using alkali metal hydroxide in methanol to obtain a reaction mixture comprising a compound of Formula IV and its corresponding regioisomer a compound of Formula IVA.

The reaction mixture obtained after the hydrolysis containing the compound of Formula IV and its corresponding regioisomer a compound of Formula IVA is treated with a halogenated hydrocarbon like methylene dichloride or ethylene dichloride; acetates like ethyl acetate, propyl acetate and the like.

In one embodiment of the present invention the mixture obtained after the hydrolysis containing the compound of Formula IV and its corresponding regioisomer a compound of Formula IVA is treated with methylene dichloride.

The compound of Formula IV, which is free of its regioisomeric impurity compound of Formula IVA, is isolated by treating the reaction mixture containing the compound of Formula IV and its corresponding regioisomer a compound of Formula IVA with a solvent selected from the group consisting of an aliphatic hydrocarbon, aromatic hydrocarbon, ether solvent.

The aliphatic hydrocarbon solvent may be selected from pentane, hexane, heptane and the like.

The aromatic hydrocarbon solvent may be selected from benzene, toluene and the like.

The ether solvent may be selected from the group consisting of diethyl ether, diisopropyl ether and the like.

In one embodiment of the present invention the mixture obtained after the hydrolysis containing the compound of Formula IV and its corresponding regioisomer a compound of Formula IVA is treated with hexane to obtain compound of Formula IV, which is free of regioisomeric impurity compound of Formula IVA.

The stirring may be carried out for a period of about 1-2 hours at a temperature in the range of about 0 to 25° C. The solid isolated from hexane is compound of Formula IV free from regioisomeric impurity, compound of Formula IVA.

If required the stirring in hexane may be repeated to obtain compound of Formula IV, which is free of regioisomeric impurity, compound of Formula IVA. In hexane, the compound of Formula IV is obtained as a solid, which can be isolated in pure form; while the regioisomeric impurity compound of Formula IVA, is present in the hexane layer.

In one embodiment of the present invention the solid obtained after treatment with hexane is treated with a mixture of hydrocarbon solvent and an ester solvent.

In one embodiment of the present invention the solid obtained after treatment with hexane is treated with a mixture of hexane and ethyl acetate to obtain compound of Formula IV, which is free of regioisomeric impurity compound of Formula IVA.

In one embodiment, the present invention provides the compound of Formula IV, which is free of regioisomeric impurity compound of Formula IVA.

In one embodiment, the present invention provides use of the compound of Formula IV, which is free of regioisomeric impurity compound of Formula IVA for preparation of fingolimod compound of formula I.

The term "free of regioisomeric impurity compound of Formula IVA" is used to indicate that regioisomeric impurity compound of Formula IVA is present to the extent of less than 15%, preferably less than 10%, as determined by high performance liquid chromatography (HPLC).

In one embodiment, the regioisomeric impurity compound of Formula IVA is present to the extent of less than 5%, as determined by high performance liquid chromatography (HPLC).

In 'c' of the process for the preparation of fingolimod, the compound of Formula IV, which is free of regioisomeric impurity is subjected to acetylation to obtain a compound of Formula III. The acetylation may be carried out with acetyl halide, acetic acid, acetic anhydride in the presence of a base and organic solvent.

The acetyl halide may be selected from acetyl chloride, acetyl bromide and the like.

The base may be selected from an inorganic base or an organic base.

The inorganic base may be selected from the group consisting of alkali metal hydroxides such as sodium hydroxide, potassium hydroxide and lithium hydroxide and the like; metal carbonates such as sodium carbonate, potassium carbonate, magnesium carbonate, and calcium carbonate and the like; metal bicarbonates such as sodium bicarbonate, and potassium bicarbonate; metal hydrides such as lithium hydride, sodium hydride, and potassium hydride and the like.

The organic base may be selected from the group consisting of organic amines such as triethylamine, diisopropylethylamine, N,N-dimethylaniline, pyridine, 4-dimethylaminopyridine, 1,5-diazabicyclo[4.3.0]non-5-ene, 1,8-diazabicyclo[5.4.0]undec-7-ene, tri-n-butylamine, N-methylmorpholine and the like; alkali metal alkoxides such as sodium methoxide, sodium ethoxide, sodium-tert-butoxide, potassium methoxide, potassium ethoxide, potassium-tert-butoxide lithium methoxide, lithium ethoxide, lithium-tert-butoxide and the like. Preferably, triethylamine.

The solvent may be selected from halogenated hydrocarbon like methylene dichloride, ethylene dichloride, hydrocarbons and the like or hydrocarbon solvent like toluene, xylene and the like. Preferably, halogenated hydrocarbon.

In one embodiment in 'c' of the process for the preparation of fingolimod, the compound of Formula IV which is free of regioisomeric impurity is subjected to acetylation with acetyl chloride and in presence of triethyl amine and methylene dichloride to obtain a compound of Formula III.

In one embodiment in 'c' of the process for the preparation of fingolimod, the compound of Formula IV which is free of regioisomeric impurity is subjected to acetylation with acetic anhydride and in presence of 4-dimethylaminopyridine and toluene to obtain a compound of Formula III.

In 'd' of the process for the preparation of fingolimod, the compound of Formula III is converted to a compound of Formula VI by subjecting the compound of Formula III to reduction and deacetylation;

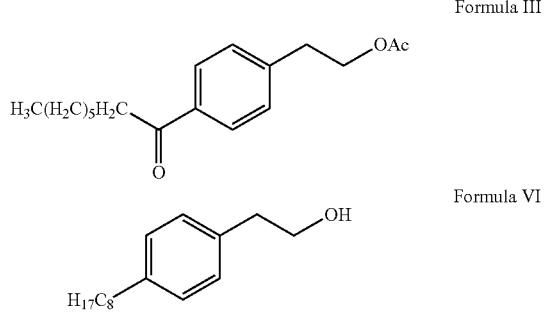

Formula III

Formula VI

The compound of Formula III may be subjected to reduction to generate the compound of Formula V.

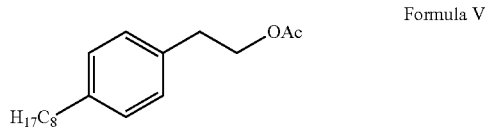

Formula V

The reduction may be carried out in the presence of reducing agents selected from the group consisting of NaBH$_4$, LiAlH$_4$, H$_2$/catalyst, ammonium formate, triethylsilane in combination with trifluoroacetic acid. The catalyst may be selected from palladium, platinum, ruthenium, rhodium, or nickel. Preferably the reducing agent is palladium on carbon.

In one embodiment, the present invention provides the compound of Formula III may be subjected to reduction by using palladium on carbon. The level of Pd-C used for hydrogenation can range from about 5% w/w to about 50% w/w, preferably about 10% w/w, based on charcoal. The palladium on charcoal used in the process described above can be of any grade available commercially.

Hydrogenation is carried out using hydrogen pressure of about 1 to 50 psi, preferably at about 10 psi to about 40 psi.

The hydrogenation is carried out in the presence of hydrogen or hydrogen transfer reagents selected from formic acid, salts of formic acid, phosphonic acid, hydrazine, monosodium dihydrogen orthophosphate, cyclohexene or mixtures thereof, where hydrogen is preferred.

The pH of the reaction may be from about 1 to about 5, preferably at pH of about 1.

The hydrogenation may be carried out in the presence of an acid. The aqueous acids that can be used may be selected from the group consisting of hydrochloric acid, acetic acid, orthophosphoric acid, trifluoroacetic acid, trifluoromethane sulfonic acid, methane sulfonic acid, nitric acid, sulfuric acid or the mixtures thereof or their aqueous mixtures, where acetic acid is preferred. The hydrogenation process may be carried out without use of any additional organic solvent.

The temperatures for conducting the reaction can range from about 25° C. to about 70° C., preferably from about 25° C. to about 50° C. and more preferably from about 30° C. to about 40° C.

In one embodiment, the present invention provides the compound of Formula III may be subjected to reduction by using palladium on carbon and hydrogen gas under pressure in presence of acetic acid to generate the compound of Formula V.

The compound of Formula V generated may be subjected to deacetylation to obtain compound of Formula VI.

The deacetylation may be carried out under acidic or basic reagents. The acidic reagents may be selected from inorganic acids like hydrochloric acid, sulfuric acid and the like and organic acids like acetic acid and the like. The basic reagents for deacetylation may be selected form hydroxides, carbonates, bicarbonates of alkali and alkaline earth metals, alkoxides for example, sodium hydroxide, potassium hydroxide, sodium carbonate, potassium carbonate, potassium bicarbonate, sodium methoxide, potassium methoxide and the like.

The deacetylation may be carried out in presence of water miscible organic solvent like lower alcohols and the like.

In one embodiment of the present invention the deacetylation is carried out by sodium hydroxide and in methanol as solvent.

In one embodiment of the present invention the compound of Formula III is converted to a compound of Formula VI by subjecting the compound of Formula III to reduction by using palladium on carbon and hydrogen gas under pressure in presence of acetic acid to generate the compound of Formula V and deacetylating the compound of Formula V with sodium hydroxide in methanol.

Since the regioisomer compound of Formula IVA is separated, the substantially pure IV is used in the subsequent reaction to obtain the compound of Formula VI in pure form, free of its corresponding regioisomer VIA. The undesired regioisomer VIA is present to the extent of less than 0.5%, as determined by high performance liquid chromatography (HPLC).

Formula VIA

[Structure: 2-(2-octylphenyl)ethanol — benzene ring with CH2CH2OH and C8H17 substituents]

The compound of Formula VI is converted to a compound of Formula IX via compounds of Formula VII and VIII Formula VII

[Structure: benzene ring with CH2CH2OSO2CH3 and H17C8 substituents]

Formula VIII

[Structure: benzene ring with CH2CH2I and H17C8 substituents]

Formula IX

[Structure: benzene ring with CH2CH2C(NHAc)(COOEt)(COOEt) and H17C8 substituents]

The compound of Formula VI is converted to a compound of Formula VII by any method known in the art, which includes, for example, by the reaction with methanesulfonyl chloride and in the presence of a base.

The base may be selected from an inorganic base or an organic base.

The inorganic base may be selected from the group consisting of alkali metal hydroxides such as sodium hydroxide, potassium hydroxide and lithium hydroxide and the like; metal carbonates such as sodium carbonate, potassium carbonate, magnesium carbonate, and calcium carbonate and the like; metal bicarbonates such as sodium bicarbonate, and potassium bicarbonate; metal hydrides such as lithium hydride, sodium hydride, and potassium hydride and the like.

The organic base may be selected from the group consisting of organic amines such as triethylamine, diisopropylethylamine, N,N-dimethylaniline, pyridine, 4-dimethylaminopyridine, 1,5-diazabicyclo[4.3.0]non-5-ene, 1,8-diazabicyclo[5.4.0]undec-7-ene, tri-n-butylamine, N-methylmorpholine and the like; alkali metal alkoxides such as sodium methoxide, sodium ethoxide, sodium-tert-butoxide, potassium methoxide, potassium ethoxide, potassium-tert-butoxide lithium methoxide, lithium ethoxide, lithium-tert-butoxide and the like. Preferably, triethylamine.

If required additional catalyst like dimethyl aminopyridine can be used.

In one embodiment of the present invention the compound of Formula VI is converted to a compound of Formula VII by reaction with methanesulfonyl chloride and in the presence of triethylamine and catalyst like dimethyl aminopyridine.

The compound of Formula VII is converted to a compound of Formula VIII by any method known in the art, for example, by the reaction with an alkali metal iodide.

In one embodiment of the present invention the compound of Formula VII is converted to a compound of Formula VIII by treatment with sodium iodide.

The compound of Formula VIII is converted to a compound of Formula IX by reacting the compound of Formula VIII with diethyl acetamidomalonate.

The reaction of compound of Formula VIII with diethyl acetamidomalonate may be carried out in the presence of a base. The base may be selected from an inorganic base or an organic base.

The inorganic base may be selected from the group consisting of alkali metal hydroxides such as sodium hydroxide, potassium hydroxide and lithium hydroxide and the like; metal carbonates such as sodium carbonate, potassium carbonate, magnesium carbonate, and calcium carbonate and the like; metal bicarbonates such as sodium bicarbonate, and potassium bicarbonate; metal hydrides such as lithium hydride, sodium hydride, and potassium hydride and the like.

The organic base may be selected from the group consisting of organic amines such as triethylamine, diisopropylethylamine, N,N-dimethylaniline, pyridine, 4-dimethylaminopyridine, 1,5-diazabicyclo[4.3.0]non-5-ene, 1,8-diazabicyclo[5.4.0]undec-7-ene, tri-n-butylamine, N-methylmorpholine and the like; alkali metal alkoxides such as sodium methoxide, sodium ethoxide, sodium-tert-butoxide, potassium methoxide, potassium ethoxide, potassium-tert-butoxide lithium methoxide, lithium ethoxide, lithium-tert-butoxide and the like.

In one embodiment of the present invention the compound of Formula VIII is converted to a compound of Formula IX by reacting the compound of Formula VIII with diethyl acetamidomalonate in the presence of sodium hydride.

The present invention provides a process for the recrystallization of the compound of Formula IX, the process comprising using a hydrocarbon solvent. The hydrocarbon solvent may be an aliphatic hydrocarbon selected from pentane, hexane, heptanes, cyclohexane and the like or aromatic hydrocarbon selected from toluene, xylene and the like.

In one embodiment, the present invention provides the recrystallization of compound of Formula IX comprising using hexane.

The present invention provides a compound of Formula IX having X-ray powder diffraction (XRPD) pattern, which is substantially in accordance with FIG. 1.

In one embodiment, the present invention provides a compound of Formula IX, free of the regioisomeric impurity compound of Formula IXA.

Formula IXA

[Structure: benzene ring with CH2CH2C(NHAc)(COOEt)(COOEt) and C8H17 substituents in ortho position]

In one embodiment, the present invention provides a compound of Formula IX, wherein the compound of Formula IXA is present to the extent of less than 0.5%, as determined by high performance liquid chromatography (HPLC).

In one embodiment, the present invention provides a compound of Formula IX wherein the compound of Formula IXA, is present to the extent of 0.1%, as determined by high performance liquid chromatography (HPLC).

In one embodiment, the present invention provides a compound of Formula IX wherein the compound of Formula IXA is absent.

In one embodiment, the present invention provides a process for preparing a compound of Formula IX which is free of its regioisomer compound of Formula IXA

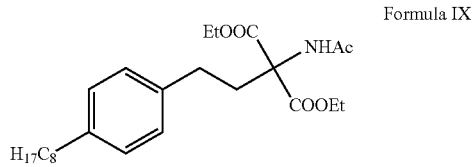

Formula IX the process comprising
a. hydrolyzing the compound of Formula III containing the regioisomer compound of Formula IIIA to obtain a reaction mixture containing the compound of Formula IV and its regioisomer compound of Formula IVA.
b. treating the reaction mixture of the compound of Formula IV and its regioisomer with hydrocarbon or ether solvent; and
c. converting the compound of Formula IV to compound of Formula IX.

The compound of Formula IV is converted to a compound of Formula IX by methods described above.

The compound of Formula IX obtained by following the process of the present invention is converted to fingolimod via a compound of Formula X.

In one embodiment, the present invention provides use of compound of formula IX free of its regioisomeric impurity compound of Formula IXA for the preparation of fingolimod or a pharmaceutically acceptable salt thereof.

In one embodiment, the present invention provides the conversion of the compound of Formula IX to Formula X, the process comprising

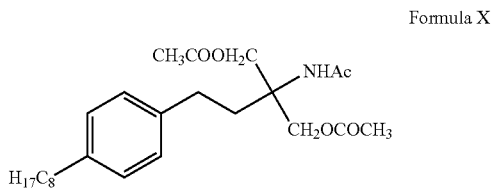

Formula X (a) reduction of carboxyl by using metal reducing agents to obtain compound of Formula XI; and

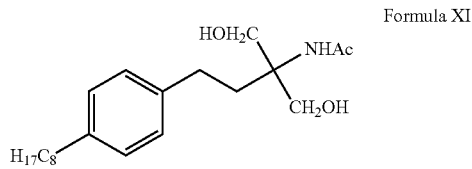

Formula XI (b) acetylating the compound of Formula XI to obtain compound of Formula X.

The metal reducing agent may be selected from the group consisting of sodium borohydride, lithium borohydride, potassium borohydride, sodium cyano borohydride, lithium aluminum hydride and diborane, lithium dimethylaminoborohydride, lithium triethylborohydride, potassium triethylborohydride, potassium triphenylborohydride, benzyltriphenylphosphonium borohydride, sodium triethylborohydride, sodium trimethoxyborohydride, tetraalkylammonium borohydride.

Preferably the reaction may be carried out in presence of metal salts are selected from calcium chloride, lithium chloride, aluminum chloride, manganese chloride, zinc chloride and the like, preferably calcium chloride.

The reduction of carboxyl by using metal reducing agents may be carried out in alcoholic solvents selected from the group consisting of methanol, ethanol, isopropanol and the like or mixtures thereof or cyclic ether solvent like tetrahydrofuran.

In one embodiment, the present invention provides the reduction of carboxyl group can be carried out by using sodium borohydride in presence of calcium chloride and in isopropanol.

The compound of Formula XI obtained by the process of the present invention may be isolated or may be further acetylated without isolation.

In one embodiment, the present invention provides the compound of Formula XI is not isolated and acetylated to obtain compound of Formula X.

The acetylation may be carried out with acetyl halide, acetic acid, acetic anhydride The acetyl halide may be selected from acetylchloride, acetyl bromide and the like.

If required, a base may be added while carrying out the acetylation. The base may be selected from an inorganic base or an organic base.

The inorganic base may be selected from the group consisting of alkali metal hydroxides such as sodium hydroxide, potassium hydroxide and lithium hydroxide and the like; metal carbonates such as sodium carbonate, potassium carbonate, magnesium carbonate, and calcium carbonate and the like; metal bicarbonates such as sodium bicarbonate, and potassium bicarbonate; metal hydrides such as lithium hydride, sodium hydride, and potassium hydride and the like.

The organic base may be selected from the group consisting of organic amines such as triethylamine, diisopropylethylamine, N,N-dimethylaniline, pyridine, 4-dimethylaminopyridine, 1,5-diazabicyclo[4.3.0]non-5-ene, 1,8-diazabicyclo[5.4.0]undec-7-ene, tri-n-butylamine, N-methylmorpholine and the like; alkali metal alkoxides such as sodium methoxide, sodium ethoxide, sodium-tert-butoxide, potassium methoxide, potassium ethoxide, potassium-tert-butoxide lithium methoxide; lithium ethoxide, lithium-tert-butoxide and the like. Preferably, triethylamine.

The acetylation of the compound of Formula XI to obtain compound of Formula X may be carried out in a solvent.

The solvent may be selected from halogenated hydrocarbon like methylene dichloride, ethylene dichloride, hydrocarbons and the like or hydrocarbon solvent like toluene, xylene and the like. Preferably, halogenated hydrocarbon.

In one embodiment, the present invention provides the acetylation of compound of Formula XI to obtain compound of Formula X may be carried out by acetic anhydride and using 4-dimethylaminopyridine in methylene dichloride.

The compound of Formula X is converted to fingolimod, compound of Formula I, by use of base such as an alkali metal hydroxide like sodium hydroxide, potassium hydroxide, lithium hydroxide or alkaline earth metal hydroxide such as calcium hydroxide, magnesium hydroxide and the like.

The reaction may be carried out in aqueous medium or mixture of aqueous and organic solvent.

In one embodiment, the present invention provides the compound of Formula X is converted to fingolimod, compound of Formula I, by use of sodium hydroxide in mixture of alcohol and water.

The present invention provides fingolimod, compound of Formula I having X-ray powder diffraction (XRPD) pattern, which is substantially in accordance with FIG. 2.

In one embodiment, the present invention provides fingolimod or a pharmaceutically acceptable salt free of regioisomeric impurity compound of Formula IA or salt thereof.

The term "free of regioisomeric impurity" means that compound of Formula IA is present to an extent of less than 0.15% as determined by high performance liquid chromatography (HPLC). Preferably the regioisomeric compound of Formula IA is present to an extent of less than 0.05%, more preferably regioisomeric compound of Formula IA is present to an extent of less than 0.01%.

In one embodiment, the present invention provides fingolimod or a pharmaceutically acceptable salt with content of regioisomeric impurity compound of Formula IA or salt thereof below detection limit (BDL) as determined by high performance liquid chromatography HPLC.

In one embodiment, the present invention provides fingolimod or a pharmaceutically acceptable salt free of regioisomeric impurity compound of Formula IA or salt thereof, with purity data of at least 98.5% and regioisomer content of less than 0.15% as determined by high performance liquid chromatography (HPLC).

In one embodiment, the present invention provides fingolimod or a pharmaceutically acceptable salt free of regioisomeric impurity compound of Formula IA, IIIA, IVA, IXA.

The fingolimod obtained by following the process of the present invention may be converted to its pharmaceutically acceptable salt.

The present invention provides a process for preparing fingolimod hydrochloride by reacting fingolimod with hydrochloric acid.

The reaction of fingolimod with hydrochloric acid may be carried out in an alcoholic solvent.

The alcoholic solvent may be selected from the group consisting of methanol, ethanol, isopropanol or mixtures thereof.

In one embodiment of the present invention the fingolimod is converted to its hydrochloride salt by treatment with hydrochloric acid in ethanol.

In one embodiment, the present invention provides the fingolimod is converted to its hydrochloride salt by treatment with hydrochloric acid in methanol.

The present invention provides a process for the recrystallization of fingolimod hydrochloride, the process comprising solvent-antisolvent addition.

The solvent may be selected from an alcoholic solvent like methanol, ethanol, propanol, isopropanol, butanol, isobutanol and the like or mixtures thereof.

The antisolvent may be selected from an ester solvent like ethyl acetate, t-butyl acetate and the like. The antisolvent may be added to the solution of fingolimod in alcoholic solvent at room temperature or higher.

In one embodiment of the present invention, fingolimod hydrochloride in an alcoholic solvent is heated in the temperature range of about 50° C. to about 70° C. and an ester solvent is added at that temperature. The reaction mixture obtained was cooled to obtain crystalline fingolimod hydrochloride.

In one embodiment of the present invention fingolimod hydrochloride in ethanol is heated in the temperature range of about 50° C. to about 70° C. and ethyl acetate is added to it. The reaction mixture obtained was cooled to obtain crystalline fingolimod hydrochloride.

The present invention provides a process for the recrystallization of fingolimod hydrochloride, the process comprising using a solvent system comprising methanol and an ester solvent.

In one embodiment, the present invention provides fingolimod hydrochloride in methanol is heated in the temperature range of about 50° C. to about 70° C. and ethyl acetate is added to it. The reaction mixture obtained was cooled to obtain crystalline fingolimod hydrochloride.

The present invention provides crystalline fingolimod hydrochloride, having an X-ray powder diffraction (XRPD) pattern, which is substantially in accordance with FIG. 3.

The present invention provides crystalline fingolimod hydrochloride, having water content less than 1% Preferably the water content is less than 0.5%.

The crystalline salts of fingolimod hydrochloride and intermediates thereof of the present invention are characterized by X-ray powder diffraction, which were performed on a Philips X'pert PRO Diffractometer using Cu Kα radiation (Cu Kα1=1.54060 Å). The X-ray source is operated at 45 kV and 40 mA. Spectra are recorded at start angle from 2° to 50° 2θ, a step size 0.0167° with a time per step of 1000 seconds.

The water content was measured by Karl Fischer analysis.

In one embodiment, the present invention provides an amorphous fingolimod hydrochloride.

In one embodiment, the present invention provides a process for the preparation of amorphous fingolimod hydrochloride in isolated form, comprising:
a) providing a solution of fingolimod hydrochloride in a solvent,
b) isolating amorphous fingolimod hydrochloride from the solution obtained in (a).

The solution may be optionally filtered to remove any undissolved material.

Fingolimod hydrochloride in amorphous form may be isolated from the solution by removing the solvent from the solution by solvent distillation, spray drying, fluid bed drying, lyophilization, flash drying, spin flash drying, or thin-film drying.

In one embodiment, the present invention provides amorphous fingolimod hydrochloride, which is isolated from the solution by spray drying. The solution of fingolimod hydrochloride is fed into a spray drier. The feed rate and inlet and outlet temperatures may be adjusted for desired output. The amorphous fingolimod hydrochloride collected from the spray dryer may optionally be further dried under vacuum to reduce residual solvent content.

In another embodiment, the present invention provides amorphous fingolimod hydrochloride, which is isolated from the solution by fast evaporation which involves solvent distillation under reduced pressure. The solution of fingolimod hydrochloride is fed into a rotavapor and the solvent is removed.

In one embodiment, the present invention provides amorphous fingolimod hydrochloride, which is isolated from a solution of fingolimod hydrochloride in a solvent by treating the solution of fingolimod hydrochloride with an antisolvent.

In one embodiment, the present invention provides a method of determining the amount of an impurity in a sample of fingolimod or pharmaceutically acceptable salt thereof comprising chromatographic measurement using gas chromatography (GC) or high performance liquid chromatography (HPLC); the determination comprising measuring the area under a peak corresponding to regioisomer compound of Formula IA in a reference standard that comprises a known amount of regioisomer compound of Formula IA; measuring by HPLC or GC the area under a peak corresponding to regioisomer compound of Formula IA in a sample comprising regioisomer compound of Formula IA and fingolimod or pharmaceutically acceptable salt thereof; and determining the amount of the regioisomer compound of Formula IA in the sample by comparing the area of reference standard with that of the test sample.

In one embodiment, the present invention provides an analytical determination process for the determination of degree of regioisomer compound of Formula IA content in fingolimod, the process comprising using regioisomer compound of Formula IA as a reference standard for determining the amount of regioisomer compound of Formula IA in fingolimod, comprising using a chromatographic method to measure the area under a peak corresponding to regioisomer compound of Formula IA in a reference standard, the reference standard comprising a known amount of the regioisomer compound of Formula IA; and determining the level of regioisomer compound of Formula IA in the sample by comparing the measured area of the peak to the area under a peak measured in a sample comprising fingolimod or pharmaceutically acceptable salt thereof contaminated with regioisomer compound of Formula IA.

In one embodiment, the present invention provides fingolimod hydrochloride having bulk density of 0.28 g/ml.

In one embodiment, the present invention provides fingolimod hydrochloride having tapped density of 0.34 g/ml.

Particle size distribution is necessary in pharmaceuticals as these relate to compactness and dissolution. The D10, D50, and D90 values are useful ways for indicating a particle size distribution. D90 is a size value where at least 90 percent of the particles have a size smaller than the stated value. Likewise D10 refers to 10 percent of the particles having a size smaller than the stated value. D50 refers to at least 50 percent of the particles having a size smaller than the stated value. Methods for determining D10, D50, and D90 include those using laser light diffraction with equipment sold by Malvern Instruments ltd.

In one embodiment, the present invention provides fingolimod hydrochloride having particle size distribution wherein D(10): 2.975 µm, D(50): 11.126 µm; D(90): 41.639 µm.

The present invention provides an isolated compound of Formula XII having the structure or salt thereof

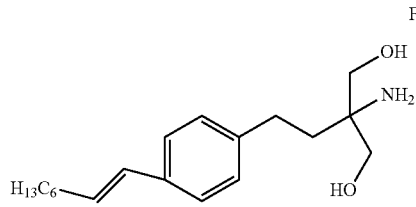

Formula XII

The present invention provides a process for the manufacture of compound of Formula XII comprising
(a) reacting a compound of Formula III with a reducing agent to form compound of Formula XIII;

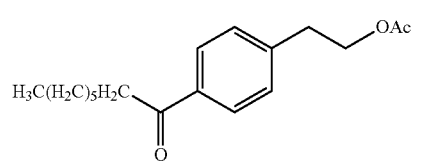

Formula III

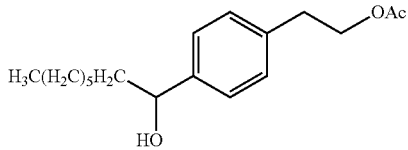

Formula XIII (b) reacting the compound of Formula XIII with dehydrating agent to form compound of Formula XIV;

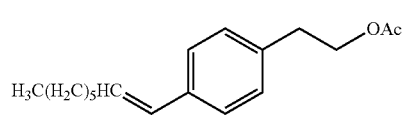

Formula XIV (c) treating the compound of Formula XIV with a base to form compound of Formula XV; and

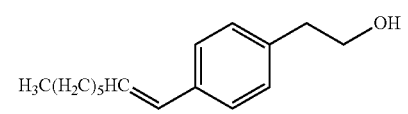

Formula XV (d) converting the compound of Formula XV to compound of Formula XII.

The reducing agent may be as described earlier. The dehydrating agent may be p-toluenesulfonic acid.

The present invention provides a compound of Formula XV is converted to compound of Formula XII by mesylation in presence of base such as triethylamine followed by halogenating with an alkali metal halide such as sodium iodide and reacting the iodo compound with diethylacetylamino malonate to form 2-(acetylamino)-2[4-[2-hexylethenyl]phenyl]ethyl]propanedioicacid diethyl ester followed by treatment with reducing agent and acetylation, and treatment with base.

The present invention provides fingolimod or a pharmaceutically acceptable salt thereof wherein compound of Formula XII is present to an extent of less than 0.1% relative to the amount of fingolimod as determined by HPLC.

In one embodiment, the present invention provides fingolimod hydrochloride free of regioisomeric impurity compound of Formula IA, IIIA, IVA, IXA and wherein compound of Formula XII is present to an extent of less than 0.1% relative to the amount of fingolimod as determined by HPLC.

In one embodiment, the present invention provides fingolimod hydrochloride free of regioisomeric impurity compound of Formula IA, IIIA, IVA, IXA and wherein compound of Formula IX, X and XI are present to an extent of less than 0.1% relative to the amount of fingolimod as determined by HPLC.

HPLC Methodology for Fingolimod HCl

Reagents, Solvents and Standards: Water (Milli Q or equivalent), Trifluroacetic acid (For Synthesis), Acetonitrile (HPLC Grade) Chromatographic Conditions: Apparatus: A High Performance Liquid Chromatograph equipped with quaternary gradient pumps, variable wavelength UV detector attached with data recorder and integrator software. Column: Inertsil ODS 3V, 250×4.6 mm, 5µ Column temperature: 30° C.; Sample cooler temperature: 25° C. Mobile Phase: Mobile Phase A=Buffer; Buffer: Adjust pH of water to 2.50 with 10% Trifluoroacetic acid in water; Mobile Phase B=Acetonitrile

| Time (min.) | % Mobile Phase A | % Mobile Phase B |
|---|---|---|
| 0.0 | 65 | 35 |
| 50 | 10 | 90 |
| 55 | 10 | 90 |
| 70 | 65 | 35 |
| 70 | 65 | 35 |

Diluent: Acetonitrile:Buffer (1:1, v/v); Flow Rate: 1.0 mL/minute Detection: UV 210 nm; Injection Volume: 20 μL Preparation of Blank solution: Mix 5 ml of acetonitrile with 5 ml of bufferPreparation of Reference solution (a): Weigh accurately about 5.0 mg each of compound of Formula XI standard, X standard, IX standard and XII standard and transfer it into a 100 ml volumetric flask. Add 50 ml of acetonitrile. Sonicate for 2-3 minutes and make up to the mark with buffer and mix. Preparation of Reference solution (b): Weigh accurately about 50.0 mg of Fingolimod Hydrochloride in-house reference standard and transfer it into a 50 ml volumetric flask. Add 25 ml of acetonitrile. Sonicate for 2-3 minutes and add 1.5 ml of reference solution (a) into it. Make up to the mark with buffer and mix. Preparation of Reference solution (c): Weigh accurately about 25.0 mg of Fingolimod Hydrochloride in-house reference standard and transfer it into a 25 ml volumetric flask. Add 13 ml of acetonitrile. Sonicate for 2-3 minutes and make up to the mark with buffer and mix. Preparation of Reference solution (d): Weigh accurately about 10.0 mg of compound of formula XII standard and transfer it into a 10 ml volumetric flask. Add 5 ml of acetonitrile and sonicate for 2-3 minutes. Make up to the mark with buffer and mix. Preparation of Reference solution (e): Transfer 5.0 ml of reference solution (c) and reference solution (d) to 50 ml volumetric flask. Add 25 ml of acetonitrile, make up to the mark with buffer and mix well. Further transfer 1.0 ml of this solution to 100 ml volumetric flask. Add 50 ml of acetonitrile, make up to the mark with buffer and mix well. Preparation of Test solution: Weigh accurately about 25.0 mg of sample and transfer it into a 25 ml volumetric flask. Add about 13 ml of acetonitrile. Sonicate for 2-3 minutes, make up to the mark with buffer and mix Procedure: Separately inject the equal volumes of blank solution, reference solution (b) and six replicate injections of reference solution (e). Then inject test solution in duplicate and record the chromatogram for all injections eliminating the peaks due to blank. The retention time of main peak i.e. Fingolimod hydrochloride is about 13.0 minutes under these conditions. Relative retention time for compound of Formula XI is about 2.5, for compound of Formula X is about 3.4, for compound of Formula IX is about 3.8, for compound of Formula XII is about 0.94 and for compound of formula 1A is 0.98 with respect to the main peak i.e. Fingolimod hydrochloride. Response factor for compound of Formula XI is 1.03, compound of Formula X is 1.10, for compound of Formula IX is 1.09 with respect to main peak i.e. Fingolimod hydrochloride.

The following examples are provided to enable one skilled in the art to practice the invention and are merely illustrative of the invention. The examples should not be read as limiting the scope of the invention as defined in the features and advantages.

EXAMPLES

Example 1

Preparation of Compound of Formula III 619 gm octanoyl chloride was charged in 3.0 lit 4 necked round bottomed flask (NRBF). 507 gm of aluminum chloride was added at about 25-30° C. The reaction mass was stirred for about 60 min and cooled to about 5° C. 250 gm of 2-Phenyl ethyl acetate was added slowly by maintaining reaction temperature at about 5-15° C. The reaction mass was stirred at about 15-20° C. for about 180 minutes. The reaction mass was quenched in ice and stirred for about 30 min. Ethyl acetate was added and stirring was continued for about 10 min. The organic layer was separated. The aq. layer was charged in 5.0 lit 4 NRBF and ethyl acetate was added and stirring was continued for about 10 min. The organic layer was separated. 1500 ml DM water was added to the combined organic layers and the reaction mass was cooled to about 15° C. The pH was adjusted to about 8 to 9 with liq. ammonia solution (~300 ml). The reaction mass was stirred for about 15 min. The organic layer was separated and washed with water and brine. The organic layer obtained was distilled out under vacuum and degassed for about 120 min under vacuum to give 470 gm of product.

Example 2

Preparation of Compound of Formula IV

In 5 Lit 4 NRBF, 410 g of the product obtained as in Example 1 was charged and 2050 ml of methanol was added. The reaction mass was stirred for about 10 min. An aqueous sodium hydroxide solution was prepared and added slowly to the reaction mass at about 20-30° C. The reaction mass was maintained at about 20-30° C. for about 180 min. The solvent was distilled out under vacuum at about 45-50° C. until a thick mass was obtained. The reaction mass was cooled and 4100 ml demineralized water was added. Methylene chloride was charged and stirred for about 10 min at about 20-30° C. The methylene chloride layer was separated and washed with water followed by washing with brine. The resultant methylene chloride layer was distilled out completely under vacuum and degassed. The reaction mass was cooled and 1000 ml hexane was charged at about 25° C. The reaction mass was stirred for about 60 min and cooled to about 0-5° C. and stirring continued for about 60 min. The slurry mass was filtered at about 0-5° C. and the wet cake was washed with 100 ml hexane. The product was dried under suction pressure for about 30 min. The wet cake (~200 gm) was charged in 1000 ml of hexane, and to which was added 20.5 ml ethyl acetate. The reaction mass was stirred for about 120 min and filtered. The wet cake was washed with 100 ml hexane and dried under suction pressure for about 30 min followed by drying the material in a vacuum tray drier at about 30-35° C. for about 6 hrs to get 150 gm of compound of Formula IV.

Example 2a

Preparation of Compound of Formula IV

In 5 Lit 4 NRBF 410 g of compound of Formula III obtained as in Example 1 was charged and 1230 ml of methanol was added. The reaction mass was stirred for about 10 min. An aqueous sodium hydroxide solution was prepared and added slowly to the reaction mass at about 10-30° C. The reaction mass was maintained at about 20-30° C. for about 90 min. The solvent was distilled out under vacuum at about 45-50° C. until a thick mass was obtained. The reaction mass was cooled and demineralized water was charged thereafter and cooled to about 5° C. 2050 ml ethyl acetate was added at about 5-15° C. and stirred for about 10 min at about 10-20° C. The ethyl acetate layer was separated and washed with water followed by washing with brine. The resultant ethyl acetate layer was distilled out completely under vacuum and degassed. The reaction mass was cooled and hexane was charged at about 25° C. and heated to about 45-50° C. and stirred for about 30 min and cooled to at about 0-5° C. and stirring continued for about 60 min. The slurry mass was filtered at about 0-5° C. and the wet cake was washed with hexane. The product was dried under suction pressure for about 30 min. The wet cake was recrystallized with 1600 ml hexane. The product was dried under suction pressure for about 30 min. The wet cake (~200 gm) was charged in 1000 ml of hexane and to which 20.5 ml ethyl acetate was added. The reaction mass was stirred for about 120 min and filtered; followed by drying the material in a vacuum tray drier at about 30-35° C. for about 6 hrs to get 210 gm of compound of Formula IV. Percent purity >99.5% by HPLC.

Example 3

Preparation of Compound of Formula III from Compound of Formula IV

In a round bottom flask, 750 ml of methylene chloride was charged and 150 gm of compound of Formula IV, obtained as in Example 2a, was added under nitrogen atmosphere. 91 gm of triethylamine was added and the reaction mass was cooled to about −5° C. to about 0° C. Acetyl chloride 47 gm was added slowly at about −5° C. to about 0° C. and the reaction mass was stirred at about −5° C. to about 5° C. for about 180 min. 450 ml demineralized water was charged at about −5° C. to about 5° C. and stirring continued for about 15 min at about the same temperature. The organic layer was separated and distilled out completely under vacuum and degassed to get 150 gm of compound of Formula III.

Example 3a

Preparation of Compound of Formula III from Compound of Formula IV

In a round bottom flask 750 ml of toluene was charged. 150 gm of compound of Formula IV, obtained by Example 2a, and 7.5 gm of 4-dimethylamino pyridine was added under nitrogen atmosphere. The reaction mass was cooled to about 15° C. and 74 gm of acetic anhydride was slowly added and the reaction mass was stirred at about 20-25° C. for about 60 min. 750 ml demineralized water was charged at about 20-25° C. and stirring was continued for about 15 min at about the same temperature. The organic layer was separated and distilled out completely under vacuum and degassed to get 160 gm of compound of Formula III. Purity of compound >99.0% by HPLC.

Example 4

Preparation of Compound of Formula V

In a clean dried 2.0 L autoclave 1000 ml of acetic acid was charged. The compound of Formula IV (100 g), obtained as in Example 2a, was added; followed by addition of 5.0 g of 10% Pd/C. The autoclave was closed and purged with nitrogen gas. Hydrogen pressure 10 kg mmHg was applied and the reaction mass was heated up to about 40° C. The reaction mass was maintained for about 120 min at about 40.45° C. under hydrogen pressure 10 kg mm/Hg. The catalyst was filtered through hyflo bed and the hyflo bed was washed with 100 ml acetic acid. The acetic acid was distilled at about 45-50° C. under vacuum and reaction mass was degassed for about 60 min at about 45-50° C. and the reaction mass was cooled to about 25-30° C. 1000 ml of water was added followed by addition of 800 ml of ethyl acetate. The ethyl acetate layer was separated and washed with 5% bicarbonate solution followed by washing with brine. The ethyl acetate layer was distilled out under vacuum and degassed to get 88 gm of compound of Formula V.

Example 5

Preparation of Compound of Formula VI

In a round bottom flask, 310 ml of methanol was added to which 105 g of compound of Formula V, obtained as in Example 4, was added. The reaction mass was cooled to about mass to about 20-30° C. and 50% sodium hydroxide was added and reaction mass was stirred at about 20-30° C. The reaction mass was concentrated under vacuum at about 45-50° C. and the residue cooled to about 25-30° C. Ethyl acetate was added to above residue and the reaction mass was stirred for about 10 min. 200 ml of water was added to reaction mass and pH of reaction mass was adjusted to about 7-8 by adding 7% sodium bicarbonate solution. The organic layer was separated and distilled out completely under vacuum and degassed to get 117 gm of compound of Formula VI.

Example 6

Preparation of Compound of Formula VII

In a round bottom flask, 600 ml of methylene chloride was charged and 100 gm of compound of Formula V, obtained as in Example 4, and 5.0 gm of DMAP and 110 gm of triethyl amine was added. The reaction mass was stirred for about 10 minutes and cooled at about 0-5° C. 75 gm of methane sulphonyl chloride was added at about 0-5° C. and the temperature of reaction mass was raised to about 25-30° C. The reaction mass was stirred at about 25-30° C. for about 1 hour and water (500 ml) was added to the reaction mass. The pH was adjusted to about 2-4 by using aq. HCl and the reaction mass was stirred for about 20 min. The organic layer was separated and washed with 7% bicarbonate solution followed by washing with brine. The organic layer was treated with charcoal and distilled out under vacuum and degassed to get 110 gm of compound of Formula VI.

Example 7

Preparation of Compound of Formula VIII

In a round bottom flask, 1320 ml of methyl ethyl ketone and 110 g of compound of Formula VI were charged. The reaction mass was stirred for about 10 min. 58.04 gm of sodium iodide was added to the reaction mass and stirred for about 10 minutes. The reaction mass was heated at about 80-85° C. for about 30 minutes and cooled at about 25-30° C. Water was slowly added to the reaction mass and stirred for about 20 minutes. The organic layer was separated and washed with 550 ml of 5% sodium metabisulphite solution. The organic layer was separated and 11 gm activated charcoal was added to the reaction mass and the reaction mass was stirred for about 30 minutes. The reaction mass was filtered though hyflo bed and the hyflo bed was washed with 110 ml of methyl ethyl ketone. The solvent was distilled out under vacuum and degassed to get 112 gm of compound of Formula VIII.

Example 8

Preparation of Compound of Formula IX

In a round bottom flask, 4000 ml of dimethylformamide (DMF) was charged under nitrogen atmosphere. 105 gm of sodium hydride was added and the reaction mass was stirred for about 10 min. The reaction mass was cooled at about 5-10° C. and 1104 gm diethylacetoamidomalonate was added slowly. The reaction mass was stirred for about 30 minutes and heated at about 40-45° C. 500 gm of compound of Formula VIII, obtained as in Example 7, was diluted with 1000 ml of DMF and added to above reaction mixture. The reaction mass was stirred at about 40-45° C. and cooled at about 25-30° C. A. Workup: 6000 ml of water was added and the reaction mass was stirred for about 10 min followed by addition of diisopropyl ether. The reaction mass was stirred for about 20 min and the organic layer was separated. The organic layer was distilled out under vacuum and degassed. The reaction mass was charged with hexane and stirred. The solid obtained was filtered and washed with hexane to get 295 g of compound of Formula IX. Purity of compound: 98.87%. B Alternative workup: 6000 ml of water was added and the reaction mass was stirred for 10 min followed by addition of 2500 ml toluene. The reaction mass was stirred for 20 min and the organic layer was separated. The organic layer was washed with 5% sodium bicarbonate solution and DM water. The organic layer distilled out under vacuum and degassed. The reaction mass was charged with hexane and stirred. The solid obtained was filtered and washed with hexane to get 295 g of compound of Formula IX. Purity of compound >97.5% by HPLC.

Example 9

Preparation of Compound of Formula X

In a round bottom flask, 800 ml of tetrahydrofuran (THF) was charged under nitrogen atmosphere. 14.0 gm of lithium aluminum hydride was added and the reaction mass was stirred for 10 min, cooled at about 0-5° C. and 15 gm of compound of Formula IX was diluted with 200 ml THF, which was slowly added in to above reaction mass. The reaction mass was stirred for about 120 minutes at about 25-30° C., filtered, distilled out filtrate under vacuum at 40-55° C., 250 ml water and 200 ml ethyl acetate was added in to residue. The reaction mass was stirred for about 20 min and the organic layer was separated. The organic layer was distilled under vacuum and 172 ml of pyridine was added in to the residue. Then 130 ml acetic anhydride was added under cooling ice and the mixture was stirred for about 16 hours at about 25-30° C. The reaction mixture was poured in to water and the pH was adjusted to 2-3 with conc. HCl and extracted with ethyl acetate. Ethyl acetate layer was washed with saturated sodium bicarbonate solution. The ethyl acetate was distilled under vacuum and 200 ml hexane was added into residue and stirred. The solid obtained was filtered and washed with hexane to get 27 g of compound of Formula X. Purity: 94.12% and regioisomer impurity: 0.58% by HPLC.

Example 9a

Preparation of Compound of Formula X

In a round bottom flask 1600 ml of isopropanol and 100 gm of compound of Formula IX, obtained as in Example 8, was charged and cooled to about 20-30° C. A solution of 77 g of calcium chloride in water was added and the reaction mass was stirred for about 10 min, followed by cooling at about 0-5° C. and 61 gm sodium borohydride in about 60 min was added to above reaction mass. The reaction mass was stirred for about 240 minutes at about 0-5° C. 500 ml of 1% aq. solution of hydrogen chloride was added and stirred for about 20 min. The reaction mass was filtered and filtrate distilled out under vacuum at about 40-55° C. 1000 ml water and 750 ml ethyl acetate were added to the residue. The reaction mass was stirred for about 20 min and the organic layer was separated. The organic layer was washed with 500 ml 10% brine solution. The organic layer was distilled out under vacuum and methylene dichloride 700 ml and dimethylaminopyridine (DMAP) 10.0 g were added. The methylene dichloride layer was cooled to about 5-15° C. 71 g acetic anhydride was slowly charged and reaction mass was stirred for about 120 min. 500 ml DM water was added at about 0-30° C. and stirred for about 30 min. The organic layer was separated and washed with 500 ml of 7% aq. sodium bicarbonate solution and DM water. The organic solvent was distilled out under vacuum and 100:800 ml ethylacetate:cyclohexane were added into the residue and heated to about 60-65° C. followed by cooling to about 10° C. The solid obtained was filtered and washed with cyclohexane to get 75 g of compound of Formula X. Purity of compound: Product >99.0%. In variant of this reaction, ethanol was used as solvent instead of isopropanol.

Example 10

Preparation of Fingolimod 19.1 gm of lithium hydroxide was dissolved in 231 ml of water and added to 25 gm of compound of Formula X, obtained as in Example 9 or Example 9a, dissolved in methanol and the mixture was reflux under heating for 120 min. The reaction mass was cooled, and 300 ml water was added and stirred. The solid obtained was filtered and washed with water to get 17.5 g of compound of Formula I. Purity: 98.5% and regioisomer impurity compound of Formula IA: 0.13% by HPLC.

Example 10a

Preparation of Fingolimod

In a round bottom flask, 55 g of sodium hydroxide and 850 ml water was charged at about 25° C. 100 gm of compound of Formula X, obtained as in Example 9 or Example 9a, in 1200 ml of methanol was added to the above mixture and the mixture was refluxed under heating for 120 min. The reaction mass was cooled, 1000 ml of water was added and stirred. The solid obtained was filtered and washed with water to get 70 g of compound of Formula I Purity of compound: Product >99.5% and Impurity compound of Formula XII: <0.1% by HPLC.

XRD Table of Fingolimod Base.

| Pos. [°2Th.] | d-spacing [Å] | Rel. Int. [%] | Pos. [°2Th.] | d-spacing [Å] | Rel. Int. [%] | Pos. [°2Th.] | d-spacing [Å] | Rel. Int. [%] |
|---|---|---|---|---|---|---|---|---|
| 2.69 | 32.87 | 0.53 | 19.74 | 4.50 | 4.70 | 31.70 | 2.82 | 3.45 |
| 3.98 | 22.19 | 100.00 | 20.83 | 4.26 | 8.11 | 35.13 | 2.55 | 0.28 |
| 7.90 | 11.19 | 0.87 | 21.67 | 4.10 | 0.68 | 35.71 | 2.51 | 0.41 |
| 11.87 | 7.45 | 1.51 | 24.64 | 3.61 | 1.04 | 37.14 | 2.42 | 0.05 |
| 15.78 | 5.61 | 0.16 | 27.29 | 3.27 | 4.29 | 38.91 | 2.31 | 0.09 |
| 17.78 | 4.99 | 0.55 | 27.69 | 3.22 | 9.33 | 42.43 | 2.13 | 0.25 |
| 18.11 | 4.90 | 0.28 | 30.43 | 2.94 | 0.74 | 35.71 | 2.51 | 0.41 |

Example 11

Preparation of Fingolimod Hydrochloride 17.0 gm of fingolimod was dissolved in (1:1) ethanol 120 ml:IPE.HCl 120 ml solutions. The reaction mass was stirred for about 30 min at room temperature; then concentrated under vacuum at about 40-45° C. 51 ml ethanol was added. The reaction mass was heated to about 50-55° C. and 200 ml ethyl acetate was added into the reaction mass. The reaction mass was cooled to about 5-10° C. and stirred for about 30 min. The solid obtained was filtered and washed with ethyl acetate to get 14.6 g of compound of Fingolimod hydrochloride. Purity 99.75% and regioisomer impurity compound of Formula IA: 0.006% by HPLC.

Example 11a

Preparation of Fingolimod Hydrochloride 100.0 gm of fingolimod was dissolved in methanol 500 ml and conc HCl 49 ml solutions. The reaction mass was stirred for 30 min at room temperature and, then concentrated under vacuum at about 40-45° C. 250 ml of methanol was added. The reaction mass was heated to about 63-70° C. and 800 ml ethyl acetate was added in to reaction mass. The reaction mass was cooled to about 20-25° C. and stirred for about 30 min. The solid obtained was filtered and washed with ethyl acetate to get 85 g of compound of Fingolimod hydrochloride. Purity 99.75% Impurity compound of Formula XII: 0.06% by HPLC.PSD: particle size distribution D(10): 6 μm, D(50): 24.2 μm; D(90): 67.5 μm. Water content: 0.29% by Karl fischer.

XRD Table of Fingolimod Hydrochloride

Example 11b

Preparation of Fingolimod Hydrochloride 100.0 gm of fingolimod was dissolved in ethanol 250 ml and conc HCl 49 ml solutions. The reaction mass was stirred for about 30 min at room temperature; then concentrated under vacuum at about 40-45° C. 250 ml of ethanol was added. The reaction mass was heated to about 65-70° C. and 800 ml ethyl acetate was added in to reaction mass. The reaction mass was cooled to about 20-25° C. and stirred for about 30 min. The solid obtained was filtered and washed with ethyl, acetate to get 85 g of compound of Fingolimod hydrochloride. Purity 99.75% and Impurity compound of Formula XII: 0.06% by HPLC.

Example 11c

Preparation of Fingolimod Hydrochloride

Fingolimod hydrochloride 100.0 gm was dissolved in 500 ml methanol at about 20-30° C. The reaction mass was filtered and the solvent was distilled out under vacuum at about 50-55° C. The reaction mass was cooled and 150 ml methanol and 1600 ml ethyl acetate was added. The reaction mass was heated to about 60-65° C. The reaction mass was cooled to about 5-10° C. and stirred for about 60 min. The solid obtained was filtered and washed with ethyl acetate. The material was dried under vacuum at about 20-30° C. to get 85 g of compound of Fingolimod hydrochloride. Purity 99.75%; Water content: 0.15% w/w. compound of formula IA: absent as determined by HPLC.

| Pos. [°2Th.] | d-spacing [Å] | Rel. Int. [%] | Pos. [°2Th.] | d-spacing [Å] | Rel. Int. [%] | Pos. [°2Th.] | d-spacing [Å] | Rel. Int. [%] |
|---|---|---|---|---|---|---|---|---|
| 2.19 | 40.29 | 0.20 | 20.20 | 4.40 | 2.29 | 30.88 | 2.89 | 0.36 |
| 3.59 | 24.60 | 100.00 | 20.50 | 4.33 | 11.13 | 31.74 | 2.81 | 0.44 |
| 7.15 | 12.36 | 5.99 | 20.68 | 4.30 | 3.10 | 32.085 | 2.78 | 0.56 |
| 10.72 | 8.26 | 18.55 | 21.49 | 4.14 | 20.48 | 32.52 | 2.75 | 0.31 |
| 12.51 | 7.07 | 0.80 | 21.97 | 4.05 | 1.82 | 33.28 | 2.69 | 0.58 |
| 13.57 | 6.52 | 0.25 | 23.33 | 3.81 | 2.24 | 33.65 | 2.66 | 0.26 |
| 14.30 | 6.19 | 0.20 | 24.05 | 3.69 | 0.46 | 34.76 | 2.58 | 0.25 |
| 15.41 | 5.75 | 6.54 | 25.11 | 3.55 | 5.31 | 35.63 | 2.51 | 0.19 |
| 17.34 | 5.11 | 0.22 | 26.65 | 3.35 | 4.94 | 36.41 | 2.46 | 0.09 |
| 17.88 | 4.96 | 3.09 | 27.77 | 3.21 | 0.19 | 37.92 | 2.37 | 0.14 |
| 18.36 | 4.83 | 0.53 | 28.77 | 3.10 | 2.09 | 39.91 | 2.25 | 0.25 |
| 19.45 | 4.56 | 0.46 | 29.30 | 3.04 | 1.08 | 41.05 | 2.19 | 0.22 |
| 19.75 | 4.49 | 0.48 | 30.32 | 2.94 | 0.18 | 41.52 | 2.17 | 0.24 |

Example 11d

Preparation of Fingolimod Hydrochloride

Fingolimod hydrochloride 100.0 gm was dissolved in 500 ml ethanol at about 20-30° C. The reaction mass was filtered and the solvent was distilled out under vacuum at about 50-55° C. The reaction mass was cooled and 250 ml ethanol and 1600 ml ethyl acetate was added. The reaction mass was heated to about 60-65° C. The reaction mass was cooled to about 5-10° C. and stirred for about 60 min. The solid obtained was filtered and washed with ethyl acetate. The material was dried under vacuum at about 20-30° C. to get 85 g of compound of Fingolimod hydrochloride. Purity 99.75% by HPLC.

Example 12

Preparation of Compound of Formula XII 640 ml ethanol was added to 2 lit 4 neck RBF. 40 g of 2-(acetylamino)-2[4-[2-hexylethenyl]phenyl]ethyl]propanedioicacid diethyl ester was added to under stirring. Calcium chloride solution (30.8 g in 160 ml water) was added to reaction mass. Reaction mass cooled 24.6 g sodium borohydride was added and stirred at about 5-10° C. The reaction mass quenched by adding HCl solution. The reaction mass was filtered and solid washed with ethanol. The filtrate was concentrated under vacuum and the residue diluted by adding water. The reaction mass extracted with ethyl acetate. Ethyl acetate layer distilled under vacuum to get 28 g residue. This residue dissolved in methylene dichloride and charged in to 500 ml 4 neck RBF. 2.3 g DMAP was charged under stirring to the reaction mass cooled to about 5-10° C. 20.2 g acetic anhydride was added to reaction mass. After complete addition, the reaction mass was stirred at about 5-10° C. for about 30 min. Reaction mass quenched by water and methylene dichloride layer was separated and distilled under vacuum get 28 g residue. The residue was purified with cyclohexane and ethyl acetate to get 18.5 g. 180 ml methanol was added to a 500 ml 4 neck RBF containing 15 g of residue. Sodium hydroxide solution was added to reaction mass. Reaction mass heated to about 60-65° C. and for about 45 min. The reaction mass was cooled and stirred for about 60 min. The solid was filtered and washed with water and dried. The solid dried to get 9.8 g of compound of Formula XII. 25 ml methanol was added in a 250 ml 4 neck RBF containing 5 g of above solid. 5 ml 15% hydrochloric acid in IPA was added to it at about 25-30° C. The reaction mass was stirred and concentrated under vacuum to get 5 g of hydrochloride of compound of Formula XII.

Example 13

Example 28 of U.S. Pat. No. 5,604,229 Comparative Purity and Regioisomer Content Data of Process of Present Invention and Process of Example 28 of U.S. Pat. No. 5,604,229

| S. No. | Stage | Intermediate Structure | HPLC purity; Regioisomer content/(Impurity) of process of present invention | HPLC purity; Regioisomer content/(impurity) e.g. 28 of US Pat. 229 |
|---|---|---|---|---|
| 1 | Formula III | $H_3C-(CH_2)_6-C(O)-C_6H_4-CH_2CH_2-OAc$ | HPLC purity 97.086 | 95.40% |
| 2 | Formula IV | $H_3C-(CH_2)_6-C(O)-C_6H_4-CH_2CH_2-OH$ | HPLC purity 98.61 | NA |
| 3 | Formula III | $H_3C-(CH_2)_6-C(O)-C_6H_4-CH_2CH_2-OAc$ | HPLC purity 82.00% | NA |
| 4 | Formula V | $H_{17}C_8-C_6H_4-CH_2CH_2-OAc$ | HPLC purity 90.89% Impurity: BDL | HPLC purity 77.14% Impurity: 17.36% |
| 5 | Formula VI | $H_{17}C_8-C_6H_4-CH_2CH_2-OH$ | HPLC purity 98.80% Impurity: 0.03% | HPLC purity 67.43% Impurity: 20.40% |

| S. No. | Stage | Intermediate Structure | HPLC purity; Regioisomer content/(Impurity) of process of present invention | HPLC purity; Regioisomer content/ (impurity)e.g. 28 of US Pat. 229 |
|---|---|---|---|---|
| 6 | Formula VII | 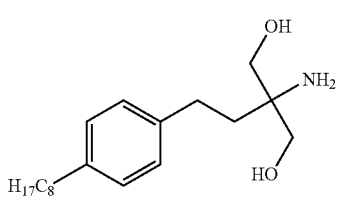 | HPLC purity 98.41% Impurity: 0.1% | HPLC purity 69.20% Impurity: 15.14% |
| 7 | Formula VIII | 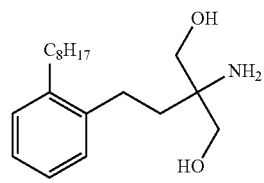 | HPLC purity 99.7% Impurity: 0.12% | HPLC purity 77.60% Impurity: 21.17% |
| 8 | Formula IX | | HPLC purity 98.87% Impurity: 0.26% | HPLC purity 88.49% Impurity: 8.48% |

BDL: Below Detection Level; Impurity: Corresponding Regioisomer Impurity; NA—Not Available Comparative Example using the process of Example 28 of U.S. Pat. No. 5,604,229 gave compound of Formula IX, wherein the regioisomer compound of Formula IX A was present to the extent of 8.5%. The compound of Formula IX obtained by following the process of U.S. Pat. No. 5,604,229 was impure and further reaction to obtain fingolimod was not viable.

The invention claimed is:

1. A process for preparation of fingolimod, a compound of Formula I or a pharmaceutically acceptable salt thereof, free of regioisomeric impurity compound of Formula IA Formula I Formula IA comprising:
(a) reacting a compound of Formula II with octanoyl halide to obtain a reaction mixture comprising a compound of Formula III and its corresponding regioisomer a compound of Formula IIIA;

Formula II

Formula III

Formula IIIA (b) hydrolyzing the reaction mixture resulting from step (a) to obtain a reaction mixture comprising a compound of Formula IV and its corresponding regioisomer a compound of Formula IVA; and isolating the compound of Formula IV which is free of its regioisomeric impurity compound of Formula IVA;

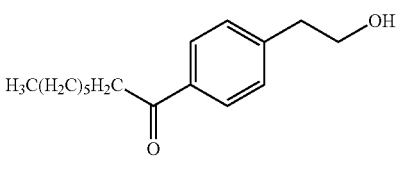

Formula IV

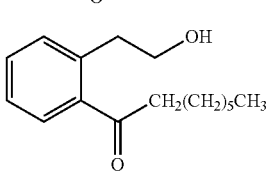

Formula IVA (c) converting the compound of Formula IV resulting from step (b) to a compound of Formula III by subjecting to acetylation;
(d) converting the compound of Formula III to a compound of Formula VI by subjecting to reduction and deacetylation;

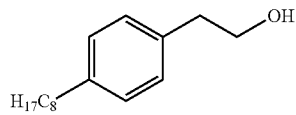

Formula VI (e) converting the compound of Formula VI to a compound of Formula IX; and

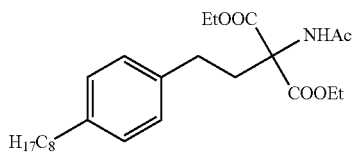

Formula IX (f) converting the compound of Formula IX to fingolimod, a compound of Formula I or pharmaceutically acceptable salt thereof.

2. A process as claimed in claim 1, for isolating the compound of Formula IV which is free of its regioisomeric impurity compound of Formula IVA, comprising treating the reaction mixture comprising a compound of Formula IV and its corresponding regioisomer a compound of Formula IVA, with a solvent selected from the group consisting of hydrocarbon solvent, ester solvent, ether solvent or mixtures thereof and isolating the compound of Formula IV which is free of its regioisomer compound of Formula IVA.

3. A process as claimed in claim 2, comprising treating the reaction mixture comprising a compound of Formula IV and us corresponding regioisomer a compound of Formula IVA, with a hydrocarbon solvent and isolating the compound of Formula IV which is free of its regioisomer compound of Formula IVA.

4. A process as claimed in claim 2, comprising treating the reaction mixture comprising a compound of Formula IV and its corresponding regioisomer a compound of Formula IVA with a mixture of hydrocarbon solvent and an ester solvent.

5. A process as claimed in claim 1, wherein in step (d) the reducing agent is selected from the group consisting of sodium borohydride, lithium aluminum hydride, $H_2$/catalyst, ammonium formate triethylsilane in combination with trifluoroacetic acid.

6. A process as claimed in claim 1, wherein the pharmaceutically acceptable salt is the hydrochloride.

7. The process of claim 2, wherein the compound of formula IV, free of its regioisomeric impurity compound of Formula IVA, is thereafter converted to fingolimod or a pharmaceutically acceptable salt thereof.

8. The process of claim 1, wherein the compound of formula IX is free of its regioisomeric impurity compound of Formula IXA and thereafter converted to fingolimod or a pharmaceutically acceptable salt thereof

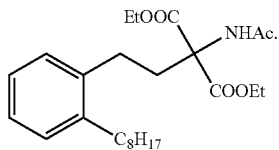

Formula IXA

9. Fingolimod or a pharmaceutically acceptable salt free of regioisomeric impurity compound of Formula IA or salt thereof as determined by HPLC

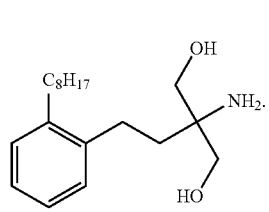

Formula 1A

10. A process as claimed in claim 1 further comprising recrystallization of fingolimod hydrochloride, using a solvent system comprising methanol and an ester solvent.

11. An isolated compound of Formula XII, having the structure

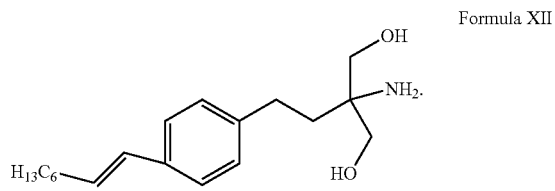

Formula XII

12. Fingolimod or a pharmaceutically acceptable salt thereof as claimed in claim 9 wherein compound of Formula XII is present to an extent of less than 0.1% relative to the amount of fingolimod as determined by HPLC

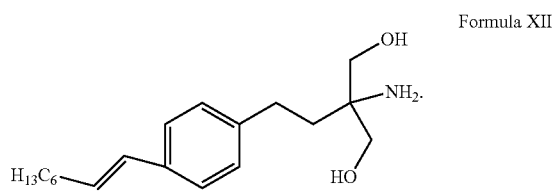

Formula XII

* * * * *